(12) United States Patent
Cluff et al.

(10) Patent No.: US 8,066,670 B2
(45) Date of Patent: *Nov. 29, 2011

(54) VASCULAR ACCESS DEVICE SEPTUM VENTING

(75) Inventors: Ken Cluff, Saratoga Springs, UT (US); Joe Frodsham, Kaysville, UT (US); Wayne K. Rasmussen, Riverdale, UT (US); Austin Jason McKinnon, Herriman, UT (US); Weston F. Harding, Lehi, UT (US); Marty L. Stout, South Weber, UT (US); Troy A. Ekberg, Sandy, UT (US); Tom M. Miner, Alpine, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 117 days.

This patent is subject to a terminal disclaimer.

(21) Appl. No.: 11/935,229

(22) Filed: Nov. 5, 2007

(65) Prior Publication Data

US 2008/0200904 A1 Aug. 21, 2008

Related U.S. Application Data

(60) Provisional application No. 60/864,510, filed on Nov. 6, 2006.

(51) Int. Cl.
*A61M 1/00* (2006.01)
(52) U.S. Cl. ........................................ 604/126; 604/122
(58) Field of Classification Search .................. 604/122, 604/126, 246, 124, 125, 167.01–167.06, 604/168.01, 236–238, 247, 533, 537–539, 256

See application file for complete search history.

(56) References Cited

U.S. PATENT DOCUMENTS

| | | | |
|---|---|---|---|
| 4,003,403 A | 1/1977 | Nehring | |
| 4,193,399 A | 3/1980 | Robinson | |
| 4,269,186 A | 5/1981 | Loveless et al. | |
| 4,682,980 A * | 7/1987 | Suzuki | 604/122 |
| 4,765,588 A | 8/1988 | Atkinson | |
| 4,894,052 A | 1/1990 | Crawford | |
| 4,917,671 A | 4/1990 | Chang | |
| 4,935,010 A * | 6/1990 | Cox et al. | 604/122 |
| 5,032,116 A | 7/1991 | Peterson et al. | |
| 5,226,883 A | 7/1993 | Katsaros et al. | |
| 5,242,411 A * | 9/1993 | Yamamoto et al. | 604/167.04 |
| 5,251,873 A | 10/1993 | Atkinson et al. | |
| 5,295,657 A | 3/1994 | Atkinson | |

(Continued)

FOREIGN PATENT DOCUMENTS

WO    WO 2004/098685 A1    11/2004

*Primary Examiner* — Kevin C Sirmons
*Assistant Examiner* — Laura Schell
(74) *Attorney, Agent, or Firm* — Mony R. Ghose; Kirton & McConkie

(57) ABSTRACT

A vascular access device may include a septum and a gas permeable vent in communication with at least a portion of the septum. The vent may be capable of venting gas from an extravascular system to which the vascular access device is capable of attaching. A method of venting a medical device may include providing a vascular access device having a septum and forming part of an extravascular system, providing a gas permeable vent in communication with at least a portion of the septum, and venting gas from the extravascular system through the gas permeable vent of the device.

13 Claims, 21 Drawing Sheets

U.S. PATENT DOCUMENTS

| | | |
|---|---|---|
| 5,295,658 A | 3/1994 | Atkinson et al. |
| 5,342,316 A | 8/1994 | Wallace |
| 5,441,487 A | 8/1995 | Vedder |
| 5,474,544 A | 12/1995 | Lynn |
| 5,501,426 A | 3/1996 | Atkinson et al. |
| 5,501,671 A | 3/1996 | Rosen et al. |
| 5,533,708 A | 7/1996 | Atkinson et al. |
| 5,542,932 A | 8/1996 | Daugherty |
| 5,549,651 A | 8/1996 | Lynn |
| 5,730,123 A | 3/1998 | Lorenzen et al. |
| 5,738,664 A | 4/1998 | Erskine et al. |
| 5,957,898 A | 9/1999 | Jepson et al. |
| 6,139,534 A | 10/2000 | Niedospial, Jr. et al. |
| 6,171,287 B1 | 1/2001 | Lynn et al. |
| 6,261,282 B1 | 7/2001 | Jepson et al. |
| 6,344,033 B1 | 2/2002 | Jepson et al. |
| 6,595,964 B2 | 7/2003 | Finley et al. |
| 6,607,513 B1 | 8/2003 | Down et al. |
| 6,651,956 B2 | 11/2003 | Miller |
| 6,669,681 B2 | 12/2003 | Jepson et al. |
| 6,866,656 B2 | 3/2005 | Tingey et al. |
| 6,908,459 B2 | 6/2005 | Harding et al. |
| 2002/0193752 A1 | 12/2002 | Lynn |
| 2005/0256500 A1 | 11/2005 | Fujii |
| 2008/0097407 A1* | 4/2008 | Plishka .......................... 604/533 |
| 2008/0103487 A1* | 5/2008 | Miyasaka ..................... 604/537 |

* cited by examiner

VASCULAR ACCESS DEVICE SEPTUM VENTING

RELATED APPLICATIONS

This application claims the benefit of U.S. Provisional Application No. 60/864,510, filed Nov. 6, 2006, entitled VASCULAR ACCESS DEVICE SEPTUM VENTING, which is incorporated herein by reference.

BACKGROUND OF THE INVENTION

The present disclosure relates to infusion therapy with vascular access devices. Infusion therapy is one of the most common health care procedures. Hospitalized, home care, and other patients receive fluids, pharmaceuticals, and blood products via a vascular access device inserted into the vascular system. Infusion therapy may be used to treat an infection, provide anesthesia or analgesia, provide nutritional support, treat cancerous growths, maintain blood pressure and heart rhythm, or many other clinically significant uses.

Infusion therapy is facilitated by a vascular access device. The vascular access device may access a patient's peripheral or central vasculature. The vascular access device may be indwelling for short term (days), moderate term (weeks), or long term (months to years). The vascular access device may be used for continuous infusion therapy or for intermittent therapy.

A common vascular access device is a catheter that is inserted into a patient's vein. The catheter length may vary from a few centimeters for peripheral access to many centimeters for central access. The catheter may be inserted transcutaneously or may be surgically implanted beneath the patient's skin. The catheter, or any other vascular access device attached thereto, may have a single lumen or multiple lumens for infusion of many fluids simultaneously. A group of vascular access and other devices used to access the vasculature of a patient may be collectively referred to as an extravascular system.

One example of an extravascular system including a catheter is the BD NEXIVA™ Closed IV (intravenous) Catheter System, by Becton, Dickinson and Company. This system includes an over-the-needle, peripheral intravascular catheter made from polyurethane, another catheter used as an integrated extension tubing with a Y adapter and slide clamp, a vent plug, a Luer access device or port, and a passive needle-shielding mechanism.

The design of the BD NEXIVA™ IV catheter can be described as a closed system since it protects clinicians or operators from blood exposure during the catheter insertion procedure. Since the needle is withdrawn through a septum that seals, after the needle has been removed and both ports of the Y adapter are closed, blood is contained within the NEXIVA™ device during catheter insertion. The pressure exerted on the needle as it passes through the septum wipes blood from the needle, further reducing potential blood exposure. The slide clamp on the integrated extension tubing is provided to eliminate blood exposure when the vent plug is replaced with another vascular access device such as an infusion set connection or a Luer access device or port.

A current procedure of initiating the use of an extravascular system such as the BD NEXIVA™ Closed IV Catheter System is as follows. A device operator inserts the needle into the vasculature of a patient and waits for flashback of blood to travel into the device to confirm that the needle is properly located within the vasculature of the patient. The blood travels into and along the catheter of the device because a vent plug permits air to escape the device as blood enters the device. After an operator confirms proper placement, the operator clamps the catheter to halt the progression of blood through the catheter, removes the vent plug, replaces the vent plug with another vascular access device such as an infusion set connection or a Luer access port, unclamps the catheter, flushes the blood from the catheter back into the vasculature of the patient, and re-clamps the catheter.

Many current procedures like the procedure described above present challenges that need to be overcome. For example, the procedure may include an unnecessary number of steps and amount of time to simply insert and prepare an extravascular system for use within the vasculature of a patient. Further, by removing the vent plug, the fluid path of the system is temporarily exposed to potential contamination from the external environment of the extravascular system.

Rather than using a vent plug, some operators attempt to solve the problem above by simply loosening a Luer access device and permitting air to escape from the system during flashback and then tightening the Luer access device to stop blood from advancing along the catheter. Unfortunately, this procedure is also prone to user error, a lack of consistent and accurate control of blood flow through the system potentially leading to blood exposure and loss of body fluids, and unnecessary risk of contamination.

Thus, what are needed are improvements to many of the systems and methods described above. Such systems and methods can be improved by providing more efficient vascular access device septum venting systems and methods.

BRIEF SUMMARY OF THE INVENTION

The present invention has been developed in response to problems and needs in the art that have not yet been fully resolved by currently available vascular access systems, devices, and methods. Thus, these systems, devices, and methods are developed to provide more efficient vascular access septum venting systems and methods.

A medical device may include a vascular access device having a septum and a gas permeable vent in communication with at least a portion of the septum. The vent may be capable of venting a gas from an extravascular system to which the device is capable of attaching.

The vent may include an adapter and a vent plug secured to the adapter, a cannula, high-density polyethylene fibers, a vent plug that is closed upon septum actuation, a porous plastic material, a porous fibrous material, a micro tube array, a laminated film vent, and/or a venting plug. The septum may include a top disc and the venting plug may at least in part encapsulate the top disc. The venting plug may also include a narrow cross section.

The septum may include a bi-stable spring which may be embedded within the material of the septum. The vent may also include a cannula and the device may include a chamber in communication with the septum, and the chamber may be filled with gel. The vent may include a needle capable of penetrating the septum.

The vent may also include a hydrophobic thread, a plastic catheter tubing, a round cannula, a flattened cannula, a cross section having a substantially symmetrical cross section with a length greater than the width of the cross, a rigid tubing and a stylet, and/or an activatable venting channel secured to the vascular access device.

A method of venting a medical device may include providing a vascular access device where the vascular access device includes a septum and forms part of an extravascular system, providing a gas permeable vent in communication with at least a portion of the septum, and venting gas from the extravascular system through the gas permeable vent of the vascular access device. The vent may include an adapter and a vent plug secured to the adapter, and the method may include removing the adapter from the vascular access device. The vent may include a vent plug, and the method may include actuating the septum and simultaneously closing the vent plug.

The method may also include inserting a cannula into the septum, inserting a venting material into the septum, piercing the septum with a needle, inserting a micro tube array into the septum, inserting a laminating film vent into the septum, inserting a thread into the septum, inserting a cross into the septum, and/or inserting a stylet into the septum.

The septum may include a top disc and the method may include encapsulating the top disc with a structure in communication with the vent. The septum may include a bi-stable spring, and the method may include actuating the bi-stable spring to close the vent. The method may also include filling a portion of the vascular access device with gel. The step of providing a gas permeable vent in communication with at least a portion of the septum may also include inserting a venting channel into the septum.

A medical device may include a means for providing access to the vascular system of a patient and a means for venting an extravascular system to which the means for providing is capable of attaching. The means for providing access to the vascular system of a patient may include a septum and may form part of the extravascular system. The means for venting the extravascular system may communicate with the septum.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

FIG. 6A is a cross section view of the vent plug of FIG. 6 in the closed position.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
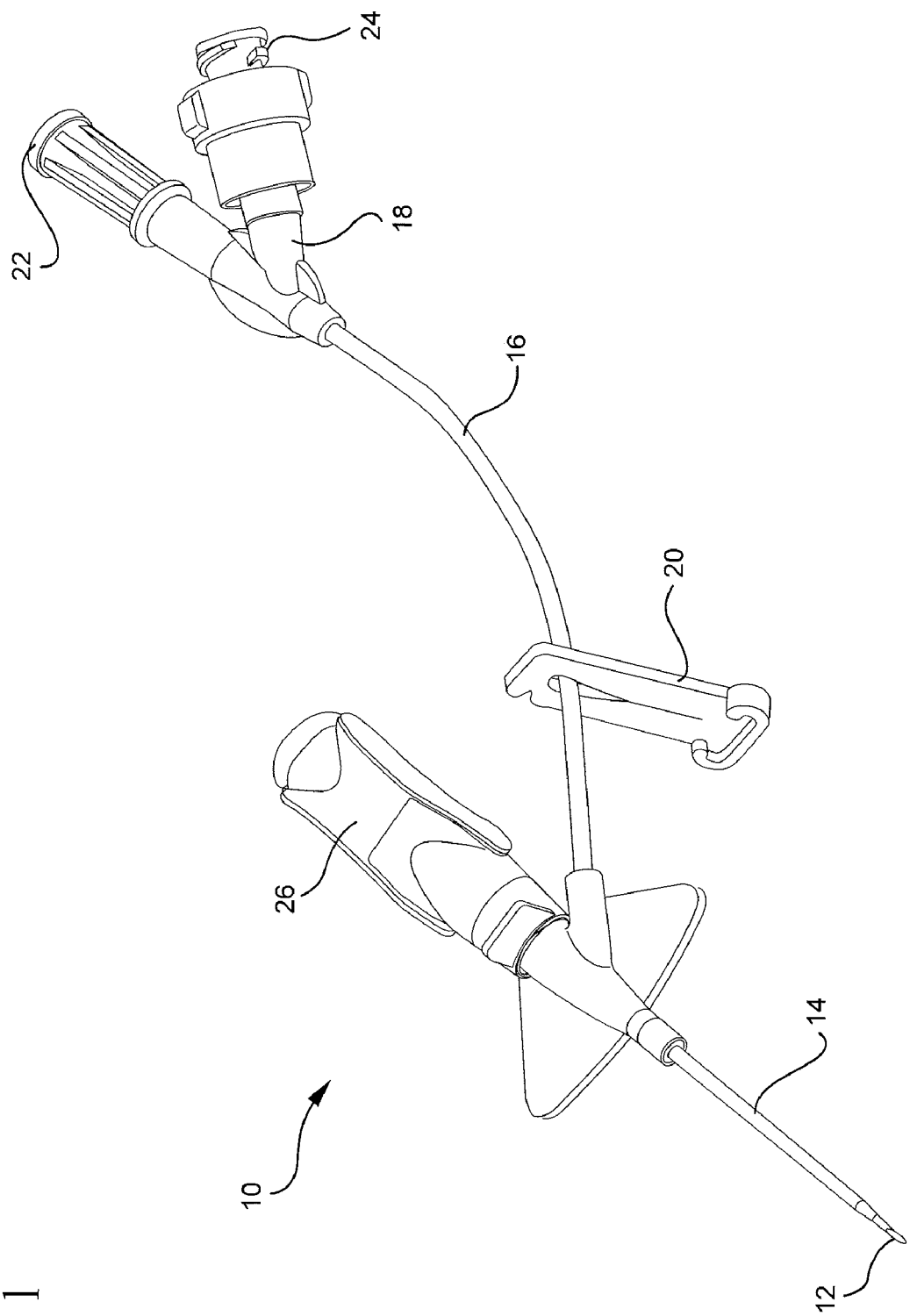
FIG. 1 is a perspective view of an extravascular system of vascular access devices.

Referring now to FIG. 1, an extravascular system 10, such as the BD NEXIVA™ Closed IV (intravenous) Catheter System, by Becton, Dickinson and Company, is used to communicate fluid with the vascular system of a patient. An example of the system 10, as shown in FIG. 1, includes multiple vascular access devices such as an intravascular needle 12; an over-the-needle, peripheral intravascular catheter 14 made from polyurethane; an integrated extension tubing 16 (also referred to herein as a catheter) with a Y adapter 18 and slide clamp 20; a vent plug 22; a Luer access device or port 24; and a passive needle-shielding mechanism 26. Any adapter used to connect two or more vascular access devices may be used in place of the Y adapter 18.

The system 10 is a closed system since it protects clinicians or operators from blood exposure during the catheter 14 insertion procedure. Since the needle 12 is withdrawn through a septum that seals after the needle 12 has been removed and both ports of the Y adapter 18 are closed, blood is contained within the system 10 during catheter 14 insertion. The pressure exerted on the needle 12 as it passes through the septum wipes blood from the needle 12, further reducing potential blood exposure. The slide clamp 20 on the integrated extension tubing 16 is provided to eliminate blood exposure when the vent plug 22 is replaced with another vascular access device such as an infusion set connection or another Luer access device or port 24.

As mentioned above, a current procedure of initiating the use of the extravascular system 10 is as follows. A device operator will insert the needle 12 into the vasculature of a patient and wait for flashback of blood to travel into the system 10 to confirm that the needle 12 is properly located within the vasculature of the patient. The blood travels into and along the catheters 14 and 16 because a vent plug 22 permits air to escape the system 10 as blood enters the system 10. After an operator confirms proper placement, and after adequate venting of the system 10 has occurred, the operator clamps the catheter 16 to halt the progression of blood through the catheters 14 and 16, removes the vent plug 22, replaces the vent plug 22 with another vascular access device such as an infusion set connection or a Luer access device similar or identical to Luer access device or port 24, unclamps the catheter 16, flushes the blood from the catheters 14 and 16 back into the vasculature of the patient, and re-clamps the catheter 16. Alternate vents and venting procedures are desired and will be discussed with reference to the figures following FIG. 1.

Figure 2:
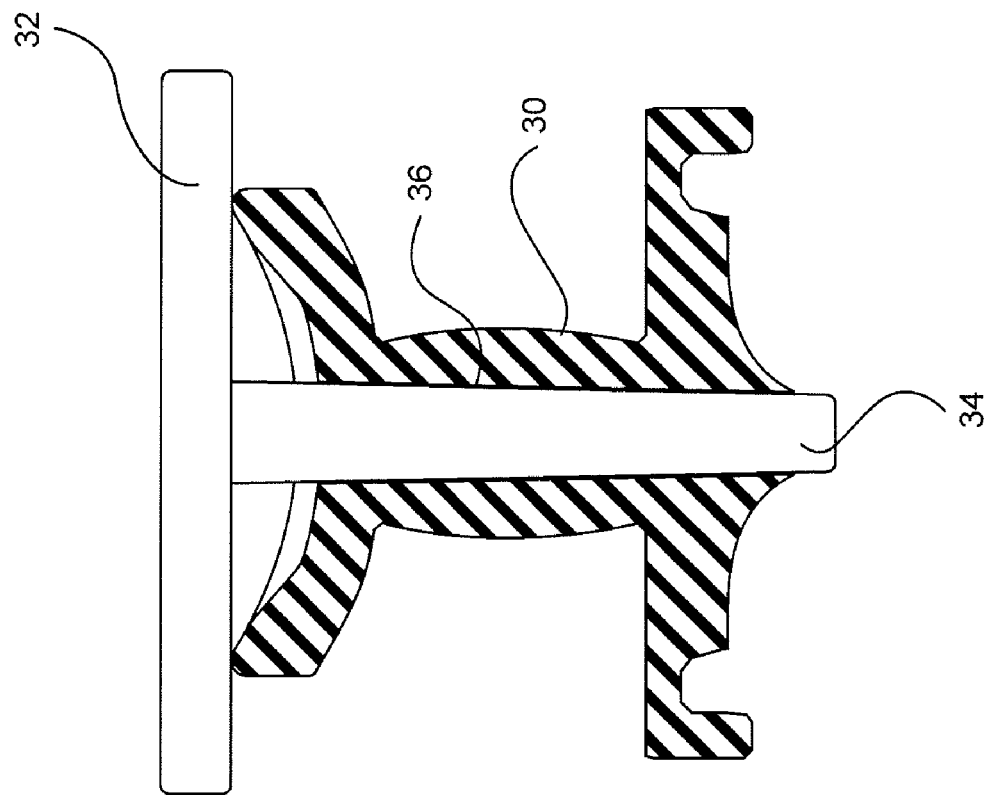
FIG. 2 is a cross section view of a septum and an adapter.

Referring now to FIG. 2, a vascular access device 28 includes a septum 30 in communication with a vent 32. The vent 32 includes an adapter that includes a Luer taper 34. The Luer taper 34 is capable of penetrating into the slit 36 of the septum 30, providing communication between the external and internal environments of the vascular access device 28.

Figure 3:
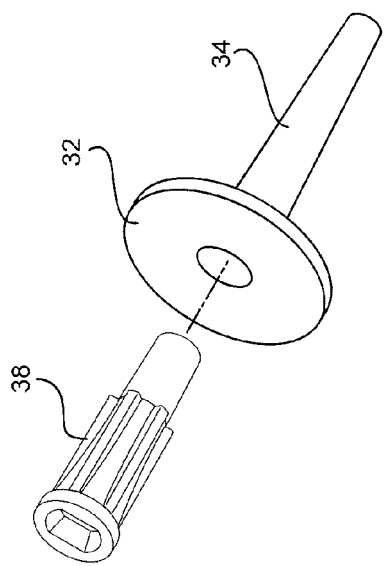
FIG. 3 is a perspective view of the adapter of FIG. 2 with a vent plug.

Referring now to FIG. 3, the adapter 32 of FIG. 2 is shown in perspective view connected to a vent plug 38. The adapter 32 includes a Luer taper 34 capable of insertion into the slit 36 of a septum 30. The vent plug 38 acts as both a gas permeable vent and a barrier to fluid between the interior of the device 28 and the external environment. The vent plug may include any venting material capable of acting as a barrier to liquid while permitting gas to permeate through the material from an internal chamber of the device 28 to the external environment in which the device 28 is placed.

Figure 4:
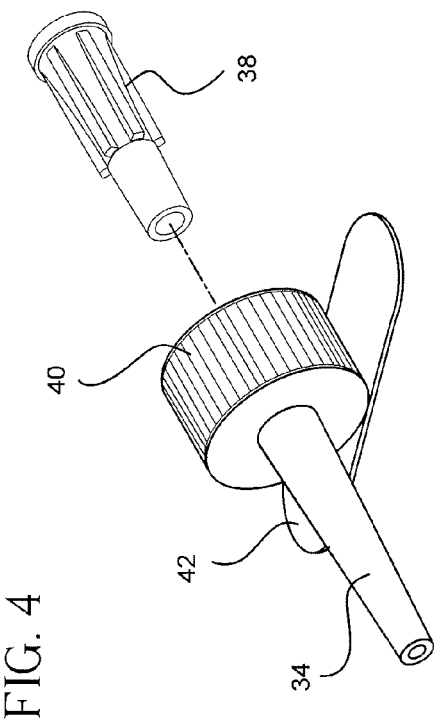
FIG. 4 is a perspective view of an alternate embodiment of an adapter and a vent plug.

Referring now to FIG. 4, an alternate adapter 40 may be combined with the vent plug 38 of FIG. 3. The alternate adapter 40 similarly includes a Luer taper 34 capable of insertion into the slit 36 of a septum 30 of a vascular access device 28 such as a Luer access device. The adapter 40 also includes wings 42 extending from the upper body of the adapter 40, so as to permit an operator to easily remove the adapter 40 after the extravascular system 10 has been fully vented of all gas through the vent plug 38. After either adapter 32 or 40 has been removed from a vascular access device 28, the septum 30 of the device 28 will close, preventing any additional liquid, such as blood, from escaping the device 28, and consequently the extravascular system 10.

Figure 5:
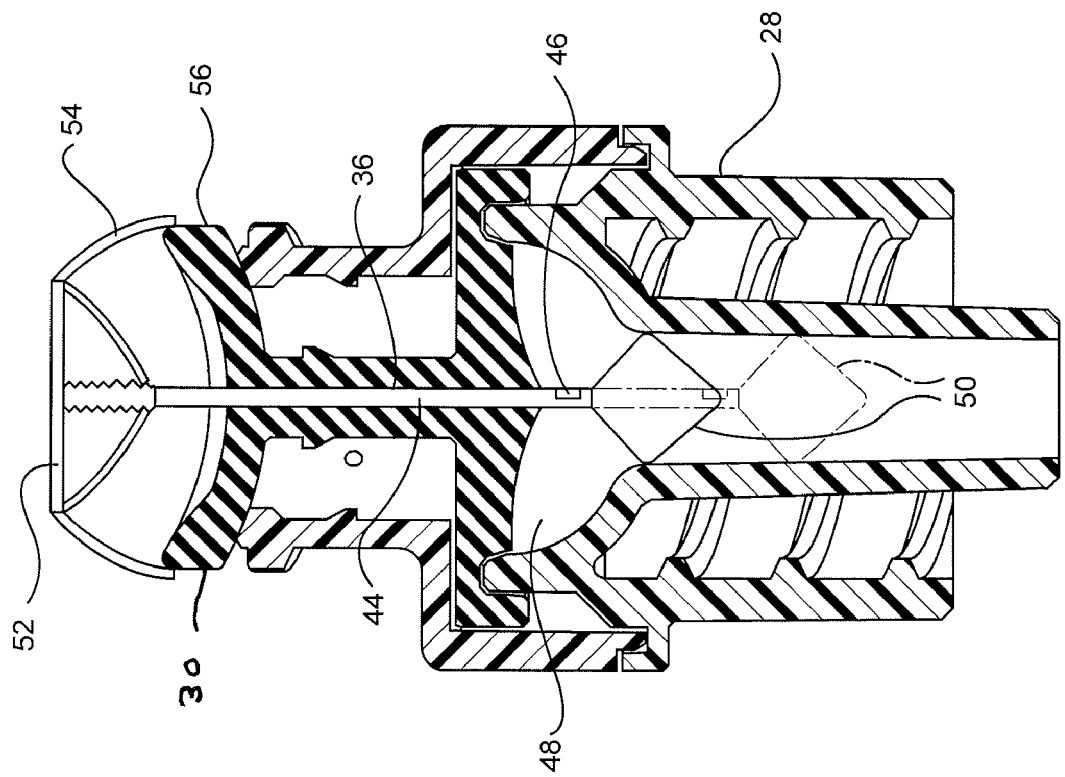
FIG. 5 is a cross section view of a vascular access device and a cannula.

Referring now to FIG. 5, a vascular access device 28 includes a septum 30 in communication with a vent. The vent includes a vented cannula 44, high-density polyethylene fibers such as those in the TYVEK® material by DuPont, or other similar material. The vented cannula 44 is located within the slit 36 of the septum 30. The vented cannula 44 includes a vent notch 46 through which gas may escape from an interior chamber 48 of the device 28 to the external environment in which the device 28 is placed. The vent notch 60, when the vented cannula 44 is fully inserted into the device 28, is located at a position below the septum 30.

Below the vent notch 46, the vented cannula 44 also includes one or more features 50 capable of exercising the septum 30 upon removal of the cannula 44 from the device 28. The purpose of the feature 50 is to ensure that the septum 30 fully recovers after the vented cannula 44 is removed therefrom. Recovery of the septum 30 requires that the two opposing surfaces of the slit 36 of the septum 30 come fully into contact with each other after removal of any device therefrom. Full recovery of the septum 30 will prevent any liquid from escaping from the interior chamber 48 to the external environment. If needed, a second and any number of additional features 50 can be added to the end of the vented cannula 44 to create a second or additional exercising of the septum 30 upon cannula 44 removal.

In addition to the one or more features 50, a biocompatible gel may be added to the surface of the features 50 to assist in sealing any hole which may exist between the two surfaces of the slit 36 in the septum 30 until the septum 30 is able to fully recover and be completely sealed. In order to ensure that the vented cannula 44 only vents gas from the interior chamber 48 to the external environment, a hydrophobic membrane 52 or other similar filter may be placed at the external end of the vented cannula which resides outside the septum 30 while the vent notch 46 resides within the interior chamber 48. The hydrophobic membrane 52 may also include a dust cover 54 capable of encapsulating or otherwise protecting the top disc 56 of the septum 30 during device 28 use. Such a protective cover 54 will help to ensure minimal infection of the sterile device 28 during use.

Figure 6:
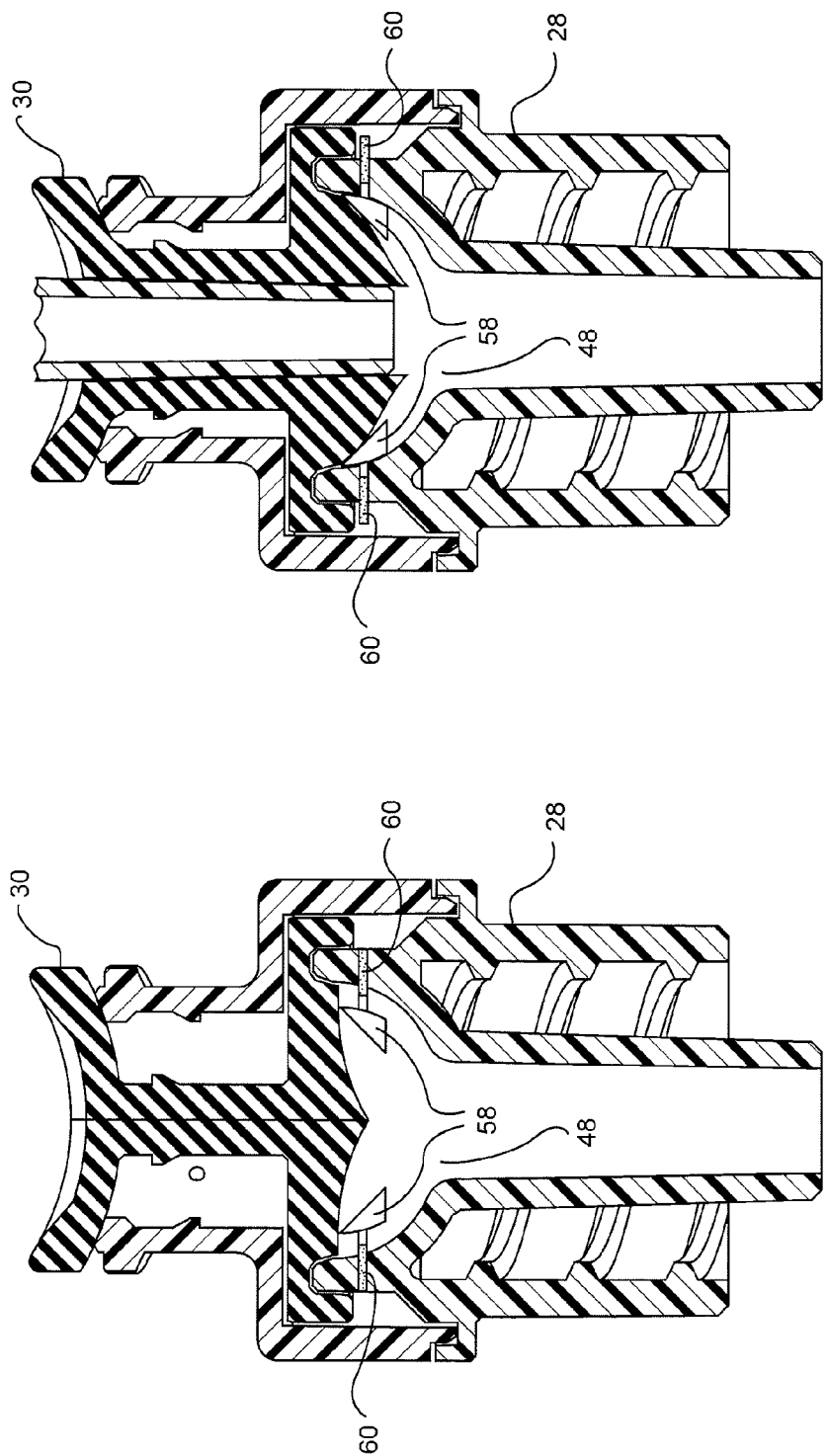
FIG. 6 is a cross section view of a vascular access device and at least one vent plug.

Referring now to FIGS. 6 and 6A, a vascular access device 28 includes a septum 30, which when accessed, is placed in communication with at least one vent plug 58. The at least one vent plug 58 may be placed anywhere on or near the septum 30 such that the vent plug 58 is capable of being closed when the septum 30 is actuated. FIG. 6A shows a first vent plug 58 on the left portion of the device 28 that has been closed as a result of septum 30 actuation. FIG. 6 also shows an open vent plug 58 on the right portion of the device 28. The open vent plug 58 permits gas to escape through a gas permeable hydrophobic portion 60 of the vent plug 58 when the vent plug 58 is not fully engaged or closed. When the vent plug 58 is fully engaged or closed, the hydrophobic portion 60 will be lodged within the body of the device 28 such that only a solid portion of the vent plug 58 is in communication with the interior chamber 48 of the device 28. The hydrophobic portion 60 may include any venting material discussed throughout this disclosure.

Figure 7:
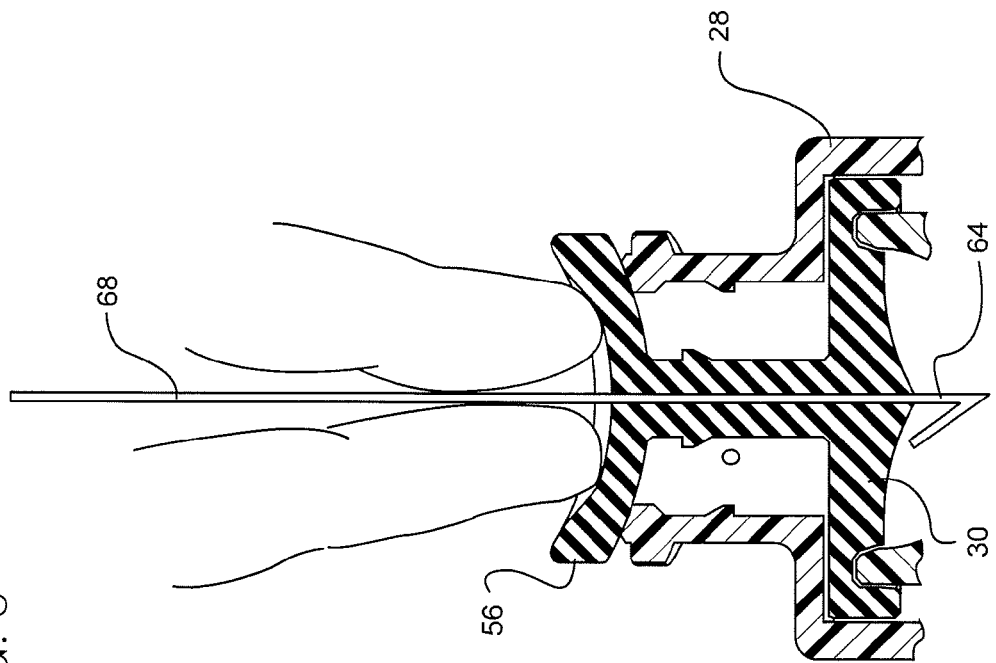
FIG. 7 is a cross section view of a vascular access device and a venting material.

Referring now to FIG. 7, a vascular access device 28 includes a vent located within the slit 36 of a septum 30 of the device 28. The vent is formed of an elongated venting material 64 such as a porous plastic material or porous fibrous material such as a Porex material, or TYVEK® material from DuPont. The venting material 64 is folded at the end that is inserted into the septum 30 in order to facilitate insertion of the material 64 at the fold 66 into the slit 36 of the septum 30.

Figure 8:
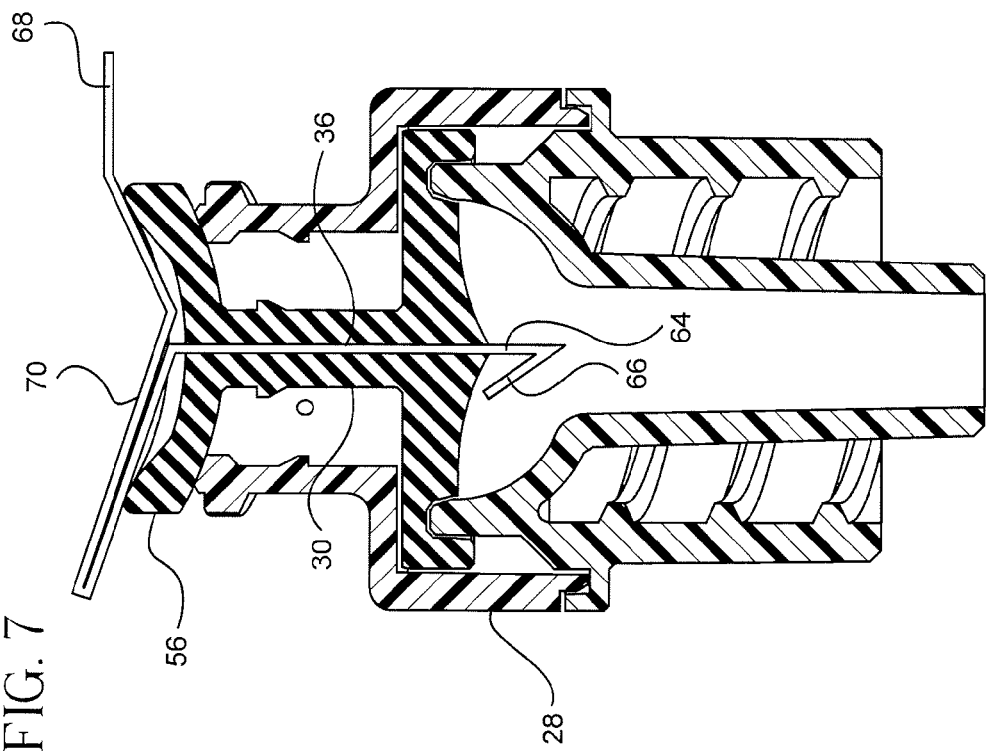
FIG. 8 is a perspective view of an operator removing a venting material from a septum.

At its opposite end, the venting material 64 may include additional folds capable of providing a pull tab 68 and a protective covering 70. The pull tab 68 provides a structure which an operator may pull in order to fully remove the venting material 64 from the device 28. The protective covering 70 is intended to act as a shield or barrier of an operator's fingers or other instruments from touching the top surface of the top disc 56 of the septum 30 during device 28 use. By acting as a protective covering, the covering 70 prevents septum 30 contamination on the face or top surface of the septum 30 that would otherwise occur or exist if the venting material 64 were pulled straight out of the slit 36 as illustrated in FIG. 8.

Figure 9:
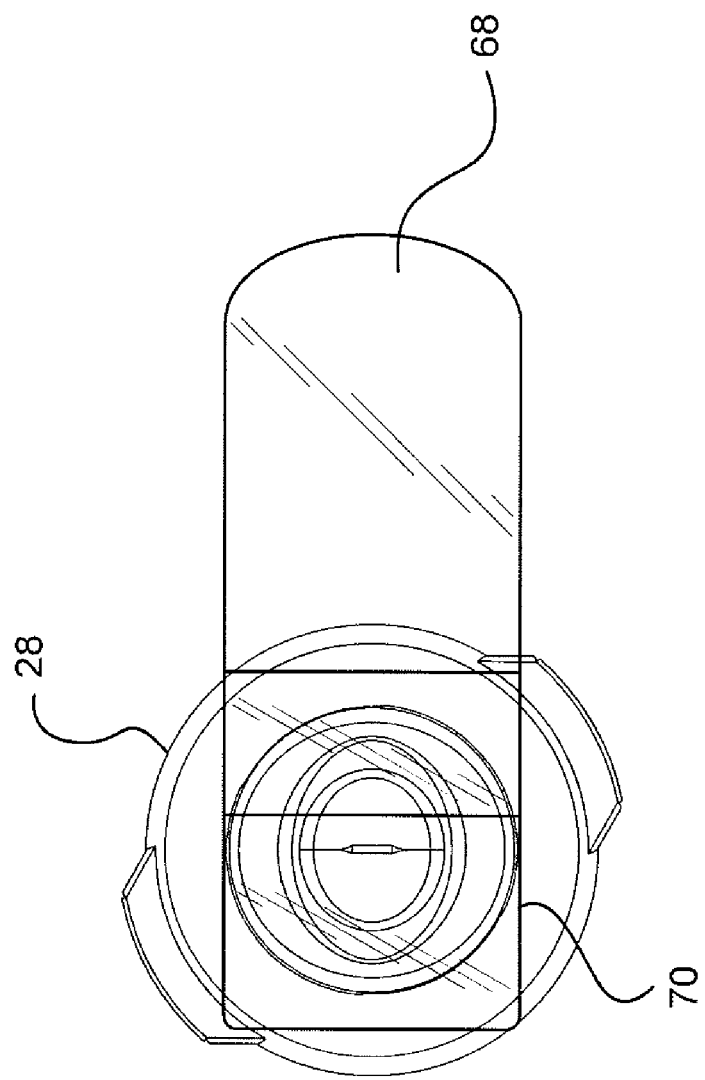
FIG. 9 is a top view of the vascular access device and venting material of FIG. 7.

Referring now to FIG. 9, a top view of the device 28 of FIG. 7 is shown. The top view reveals the pull tab 68 extending from the outer circumference of the device 28 so as to ensure that an operators fingers or other instruments do not come into contact with the septum 30. The remaining protective covering 70 also ensures that the top surface of the top disc 56 of the septum 30 is neither touched prior to or during removal of the venting material 64.

Figure 10:
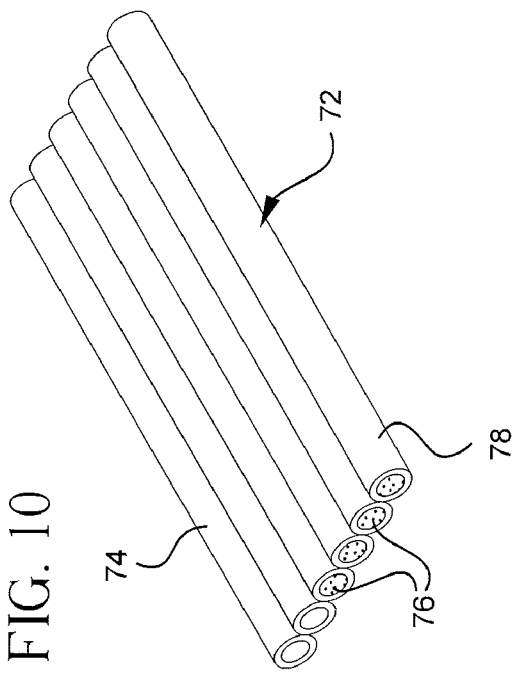
FIG. 10 is a perspective view of a micro tube array.

Referring now to FIG. 10, any other structure may be placed within the slit 36 of a septum 30 of a vascular access device 28, such as a micro tube array 72. The micro tube array 72 includes an outer structure 74 encapsulating a venting material 76, which is permeable to gas, but not liquid. Thus, the venting material 76 will permit the escape of gas from a vascular access device 28 without permitting liquid to escape from the device 28. The micro tube array 72 includes multiple microtubules 78 aligned and secured to each other in parallel.

Figure 11:
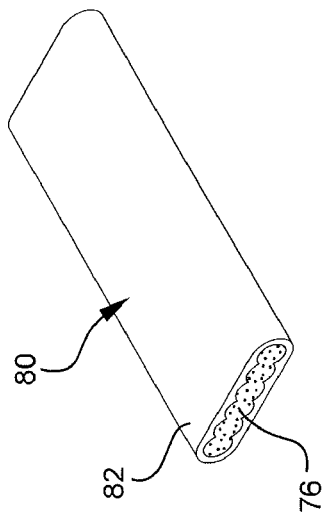
FIG. 11 is a perspective view of an integrated micro tube array.

Referring now to FIG. 11, a structure similar to the micro tube array 72 of FIG. 10 is shown as an integrated micro tube array 80. The micro tube array 80 includes multiple microtubules of venting material 76. However, the microtubules 76 are placed into contact with each other and are collectively supported and encased by an integrated casing 82.

Figure 12:
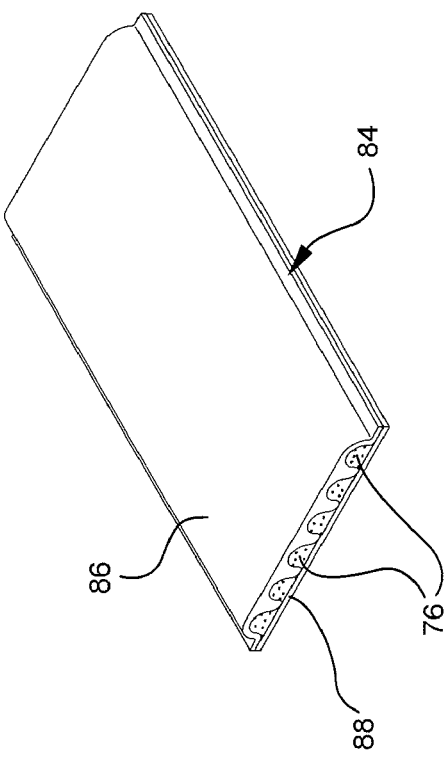
FIG. 12 is a perspective view of a laminated film vent.

Referring now to FIG. 12, a structure similar to the micro tube array 72 of FIG. 10 and the integrated micro tube array 80 of FIG. 11 is shown as a laminated film vent 84. The laminated film vent also includes multiple microtubules of venting material 76 encased within a top layer 86 that is laminated and sealed along the edges of the bottom layer 88. The top and bottom layers 86 and 88 provide support to and encompass the microtubules 76.

The supporting materials 74, 82, 86, and 88 of FIGS. 10 through 12 are not permeable to fluid. However, the microtubules 76 are permeable to gas, but not liquid. In this manner, the structures described with reference to FIGS. 10 through 12 provide a structure capable of venting a vascular access device 28 through the slit 36 of the septum 30 of the device 28.

Figure 13:
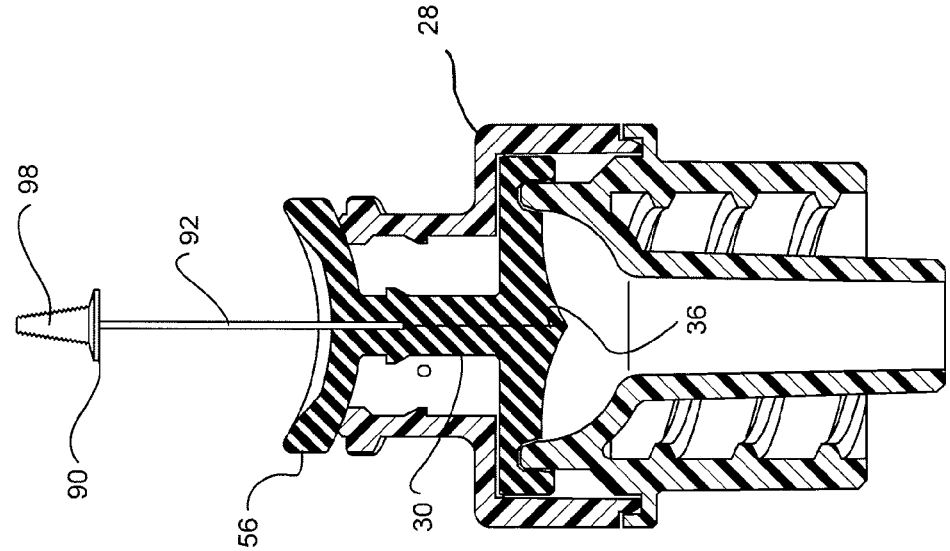
FIG. 13 is a cross section view of a vascular access device and a vent plug.

Referring now to FIG. 13, a vascular access device 28 may be combined with a venting plug 90. The venting plug 90 may include a porous strip 92 capable of insertion into the slit 36 of a septum 30 of the device 28. The porous strip 92 will be thin enough to provide adequate venting through the slit 36 without unnecessarily stressing the septum 30 in a manner that prevents a septum 30 from fully closing or otherwise sealing upon removal of the venting plug 90. To facilitate a low stress porous strip 92, a cross section of the porous strip 92 may include tapered ends or may include a thin cross section without tapered ends. The porous strip 92 is permeable to gas but not liquid, permitting air to flow from an internal chamber 48 of the device 28 to the external environment in which the device 28 is placed.

Figure 14:
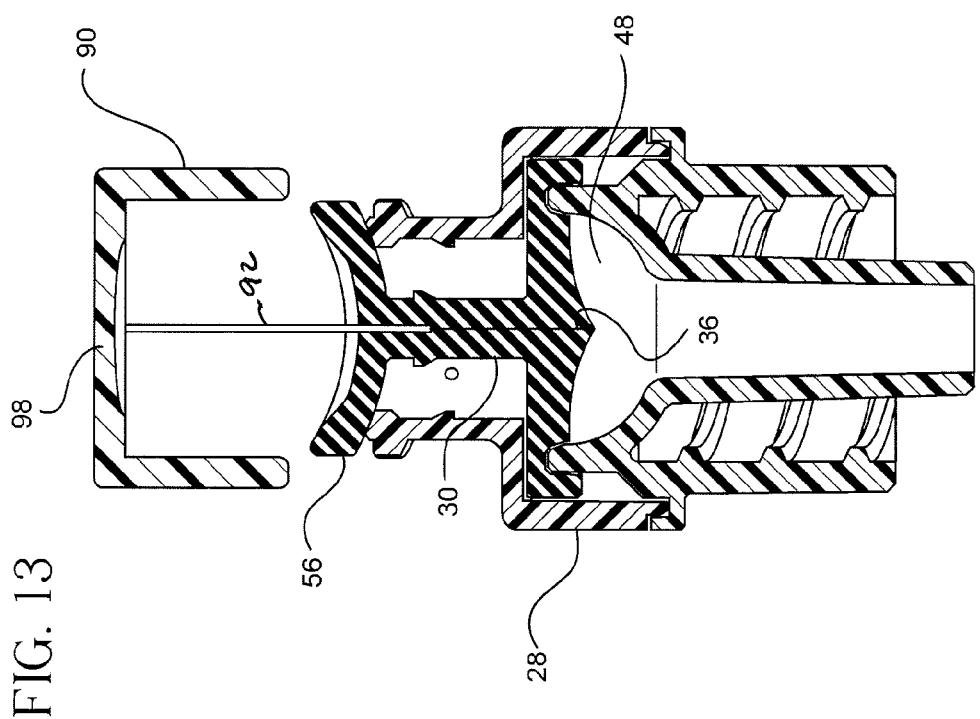
FIG. 14 is a cross section view of a vascular access device and an alternate embodiment of a vent plug.
Figure 15A:
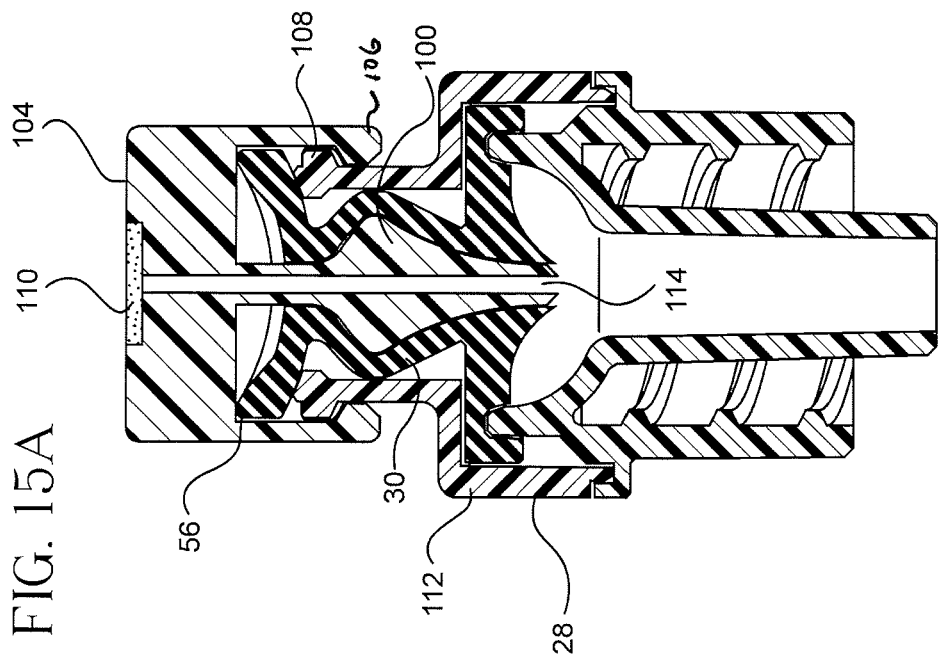
FIGS. 15-15C are cross section views of a vascular access device and multiple vent plugs and cannulas.
Figure 15:
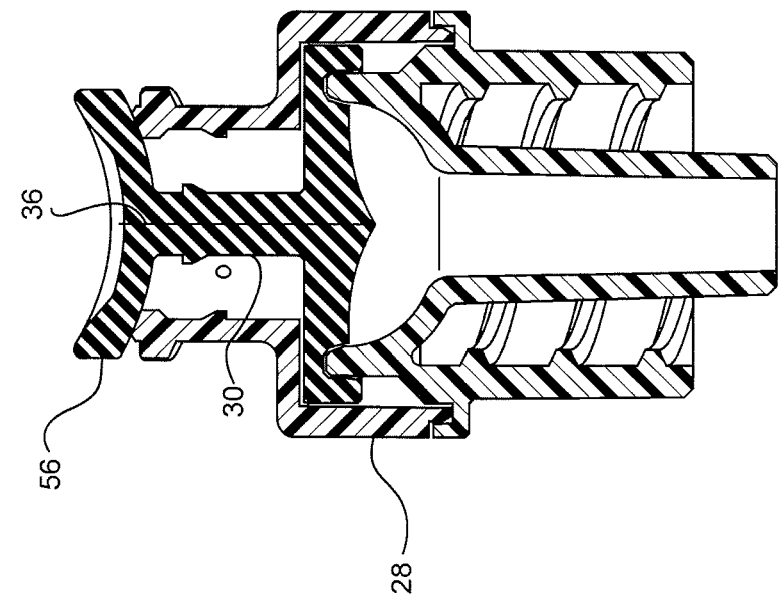
Figure 15B:
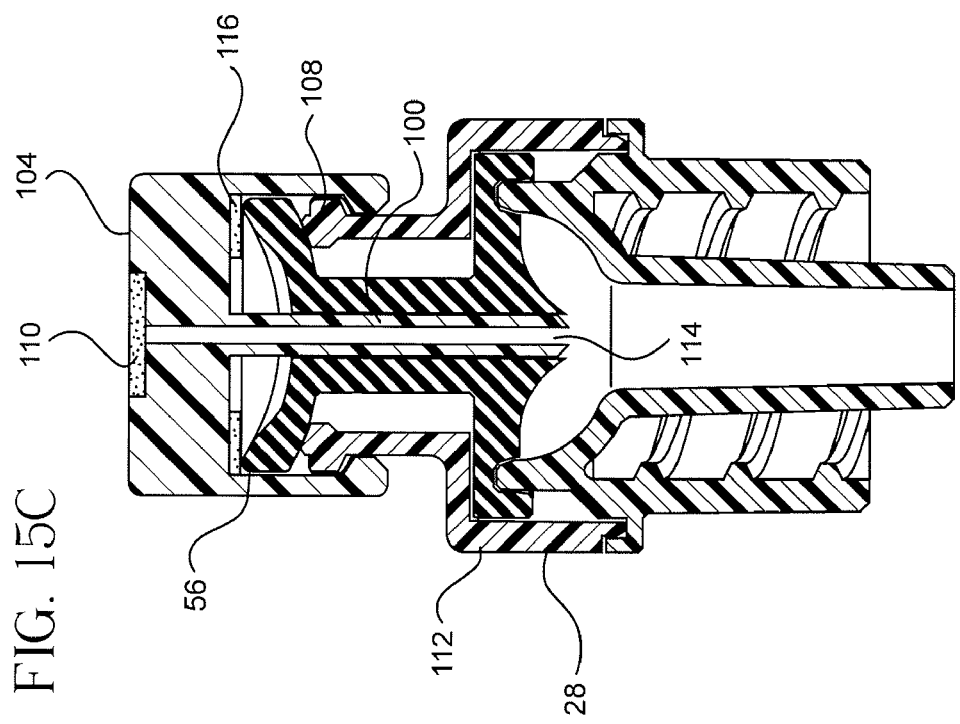
Figure 15C:
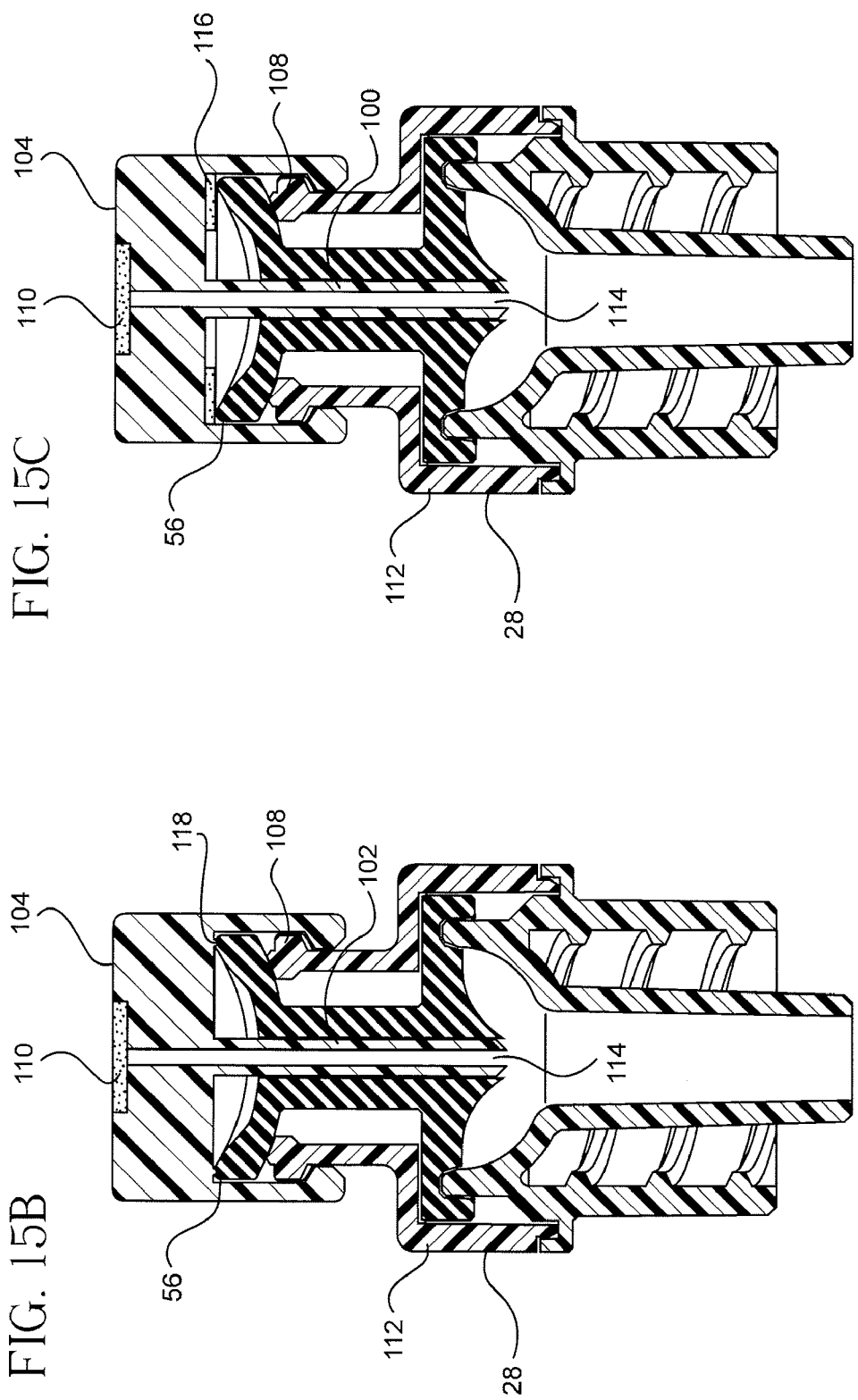

The porous strip is secured at its external end to a handle 98. The handle 98 may be a simple handle such as that shown in FIG. 14, or may be a much larger handle such as that shown in FIG. 13, capable of encapsulating the top disc 56 of the septum 30. By encapsulating the top disc 56 of the septum 30, the handle 98 provides an additional antimicrobial barrier capable of ensuring maximal device 28 sterility during the venting procedure of the extravascular system 10 to which the device 28 is attached.

Referring now to FIGS. 15, 15A, 15B, and 15C, a vascular access device 28 may include a vent with either a cannula 100 with interference housing or a small bore cannula inserted within the slit 36 of a septum 30 of the device 28. The cannulas are secured to an external end cap 104 with snap thread arms 106 capable of securing to the external threads 108 of the device 28. The end cap 104 also includes a venting plug or venting membrane 110 on its external surface capable of filtering air or other gas through the cannulas 100 and 102 while preventing the escape of liquid such as blood from the device 28. As with all venting materials in this disclosure, the vent plug or membrane 110 may include any of the venting materials discussed throughout this disclosure.

The cannula 100 with interference housing includes additional housing body along its cross section in order to add additional support and an additional sealing mechanism at a certain cross section of the device 28. Thus the interference housing of the cannula 100 will provide a continuous, sealed, connection of the body 112 of the device 28, the septum 30, and the interference housing of the cannula 100, such that only the lumen 114 of the cannula 100 provides an open space through which fluid, such as a gas, may escape.

The arms 106 may be used as a snap thread connection capable of being rapidly secured to and detached from the threads 108 of the device 28. The vent may also include a gel seal 116 between the lower surface of the body of the end cap 104 and the upper surface of the top disc 56 of the septum 30. The gel seal 116 provides an additional seal, insulator, and elastic buffer between the vent and the device 28. The gel seal 116 may be formed as a sealing ring 118 around the circumference of the bottom surface of the end cap 104.

Figure 16:
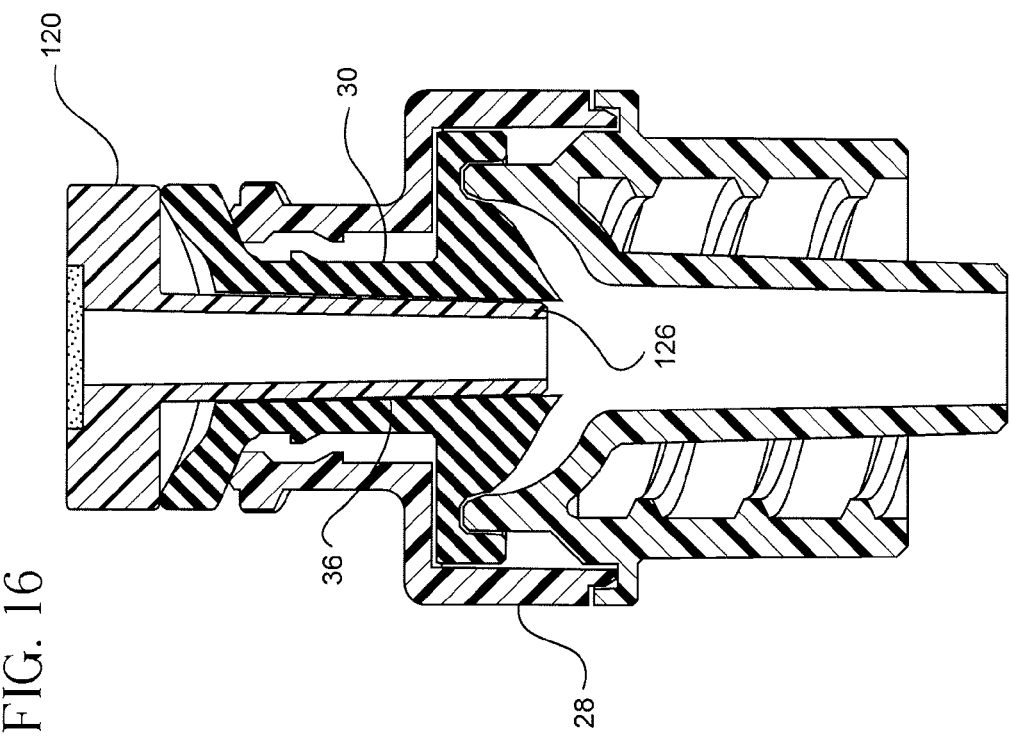
FIG. 16 is a cross section view of a vascular access device with a side view of a vent plug.

Referring now to FIG. 16, a vascular access device 28 includes a vent that includes a preinstalled venting plug 120 inserted into the slit 36 of a septum 30 of the device 28. The plug 120 may be preinstalled into the device 28 prior to operator use, and may be removed by an operator after flashback of blood is achieved within the extravascular system 10 to which the device 28 is attached during the venting procedure.

Figure 17:
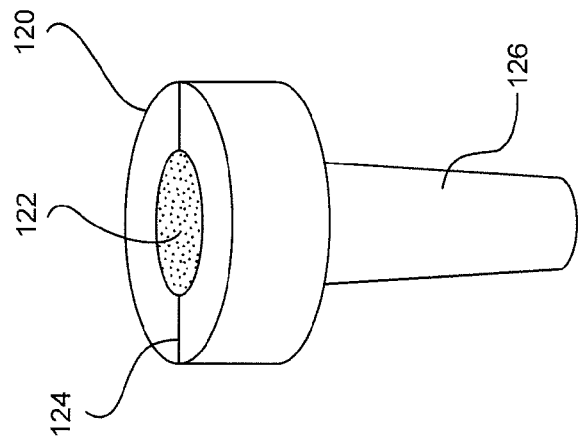
FIG. 17 is a side respective view of the vent plug of FIG. 16.

Referring now to FIG. 17, the venting plug 120 of FIG. 16 is shown in close-up view. The venting plug 120 includes a semi-permeable venting material 122 that allows gas flow but not liquid flow through the venting material 122. The venting material 122 may be any venting material discussed throughout this disclosure. The venting plug 120 may be formed in two halves by an ultrasonic weld 124 or other means of securement. The venting plug 120 may be formed of a polycarbonate or other rigid plastic or other material.

Figure 18:
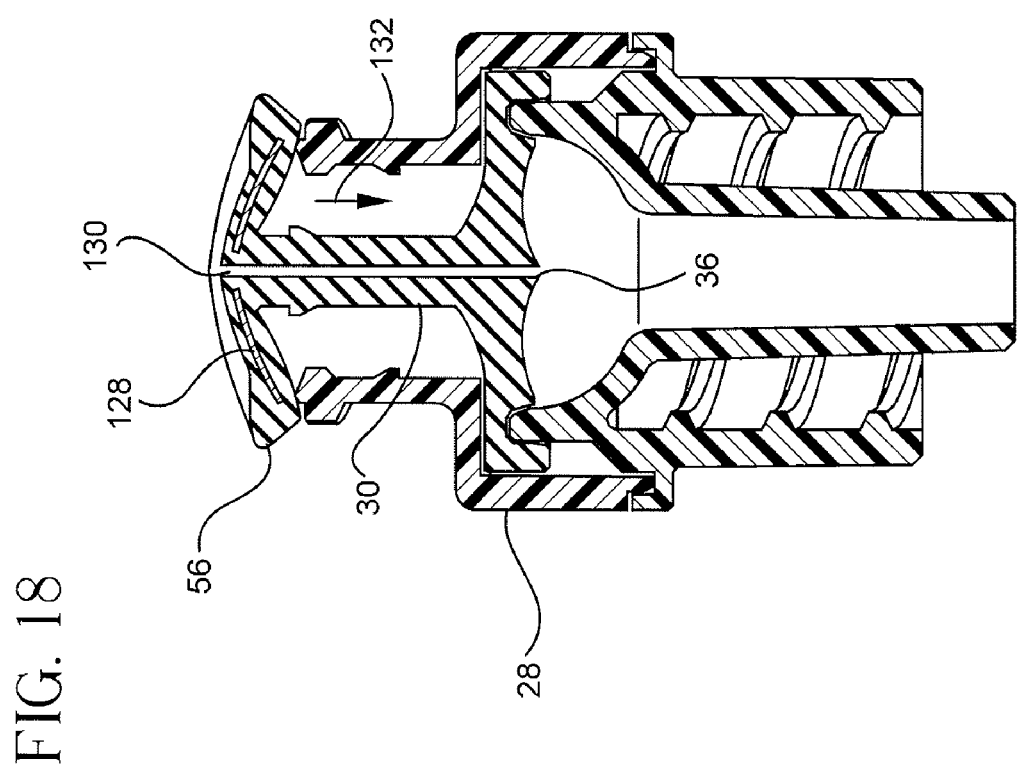
FIG. 18 is a cross section view of a vascular access device with a bi-stable spring.

Referring now to FIG. 18, a vascular access device 28 includes a septum 30 having a top disc 56 and at least one bi-stable spring 128 embedded within the top disc 56. The bi-stable spring 128 holds the septum 30 in convex position, opening an air channel 130 as a vent through which air may flow during venting of the device 28. The air channel 130 will preferably be adequately narrow such that when a liquid such as blood comes into contact with the air channel, the cohesive properties of the liquid will be bound to the surfaces of the slit 36 of the septum 30, causing the flow of liquid to slow or halt prior to its final escape into the external environment outside of the slit 36.

Upon full venting of the device 28, an operator may insert the tip of another vascular access device, such as a syringe, into the septum 30, causing the at least one bi-stable spring 128 to snap into concave position, closing the slit 36 and the air channel 130 of the septum 30. After the at least one bi-stable spring 128 has snapped or flipped into concave shape, forcing the septum 30 and top disc 56 in a downward direction 132, no further gas or liquid will be permitted to escape the device 128, and the septum 30 may be used for future access and use consistent with its purpose without reversing the at least one bi-stable spring 128 into convex shape, causing the air channel 130 to reopen.

Figure 19:
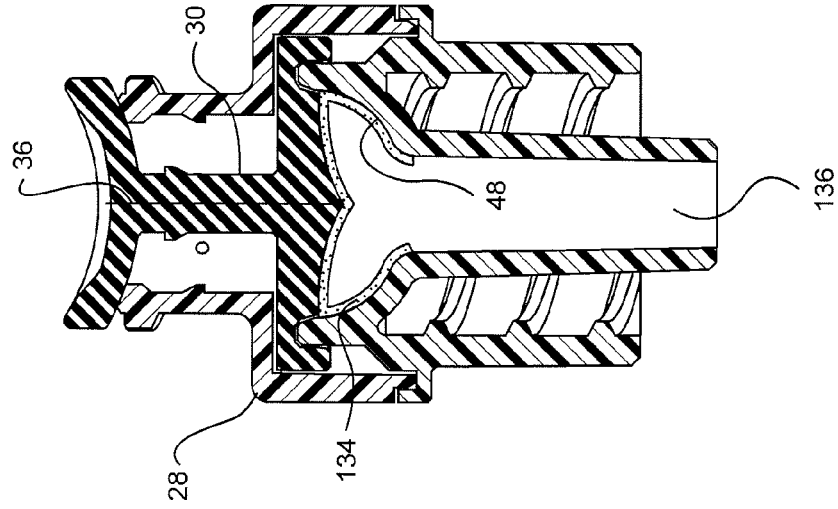
FIG. 19 is a cross section view of a vascular access device with gel.

Referring now to FIG. 19, a vascular access device of any of the embodiments of this disclosure may include a chamber 48 in communication with a septum 30. The chamber 48 may be filled with biocompatible gel 134. The device 28 may be prefilled with the biocompatible gel 134 in the chamber 48 in order to stop blood or other liquid from entering into the chamber 48 and/or other areas that are hard to flush. Areas that are hard to flush include those areas which persistently harbor trapped air bubbles or other trapped medications or fluids and later inconveniently release those air bubbles or trapped fluids at an uncontrolled rate during future use of the device 28.

The prefilled gel 134, upon initial access of the septum 30 of the device 28, is initially pushed into the fluid path 136 of the device 28 and the extravascular system 10. As the gel 134 enters into the fluid path 136, it dissolves into the surrounding intravenous fluid infused into the device 28. Any venting member, such as a cannula or other vent material or member mentioned throughout this disclosure, will extend through the slit 36 of the septum 30, through the body of gel 134, and into the end of the fluid path 136, such that the opening of the venting member is exposed to the fluid path 136.

Figure 20:
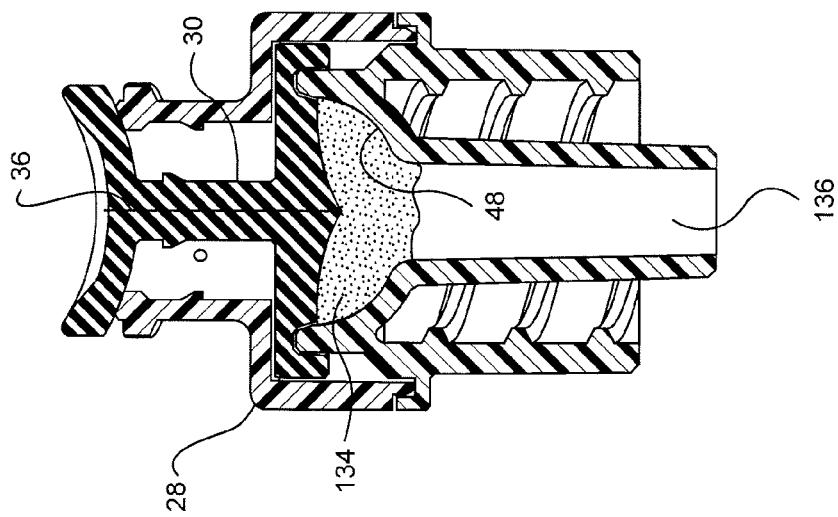
FIG. 20 is a cross section view of a vascular access device with a residue of gel.

Referring now to FIG. 20, the vascular access device 28 of FIG. 19 is shown after initial actuation of the septum 30. A layer of the gel 134 remains in order to prevent blood adhesion, unwanted trapped air bubbles, or other unwanted stagnant fluid flow after a blood draw or other use of the device 28. The layer of remaining gel 134 is coated on the inner surface of the bottom of the septum 30 and of the body of the device 28 within the chamber 48. An alternate gel material that is less solvent than the gel previously discussed may be used to more permanently reside on the surface of the chamber 48.

Figure 22:
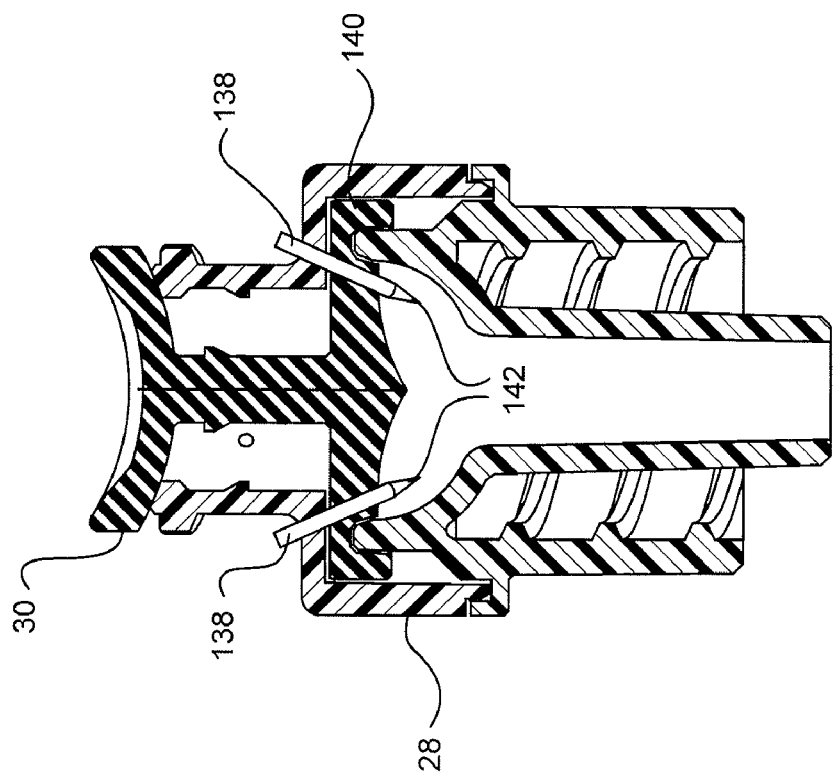
FIG. 22 is a partial cross section view of the septum of the vascular access device of FIG. 21 with the at least one needle penetrating therethrough.
Figure 21:
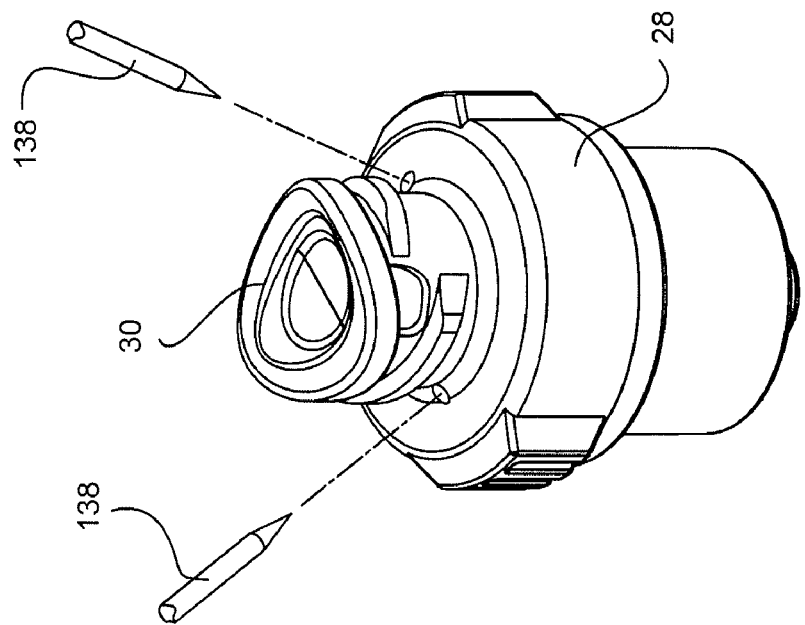
FIG. 21 is a perspective view of a vascular access device accommodating at least one needle.

Referring now to FIG. 21, a vascular access device 28 may include a vent including at least one needle 138 capable of penetrating the septum 30 of the device 28 in order to vent the extravascular system 10 to which the device 28 may be attached. The at least one needle 138 may penetrate through a molded or drilled hole within the body of the device 28 in order to penetrate through the bottom disc 140 of the septum 30, as shown in FIG. 22. The tip 142 of the at least one needle 138, having penetrated through the bottom disc 140 of the septum 30, will thus be exposed to gas residing within the device 28.

The body of the device 28 will preferably provide adequate support and lateral pressure against the bottom disc 140. Thus, after the at least one needle 138 is removed from the bottom disc 140, the hole where the at least one needle 138 penetrated through the septum 30 will fully seal and close. The sealed septum 30 will prevent any further gas or liquid from escaping through the septum 30 into the external environment in which the device 28 is placed.

Figure 23:
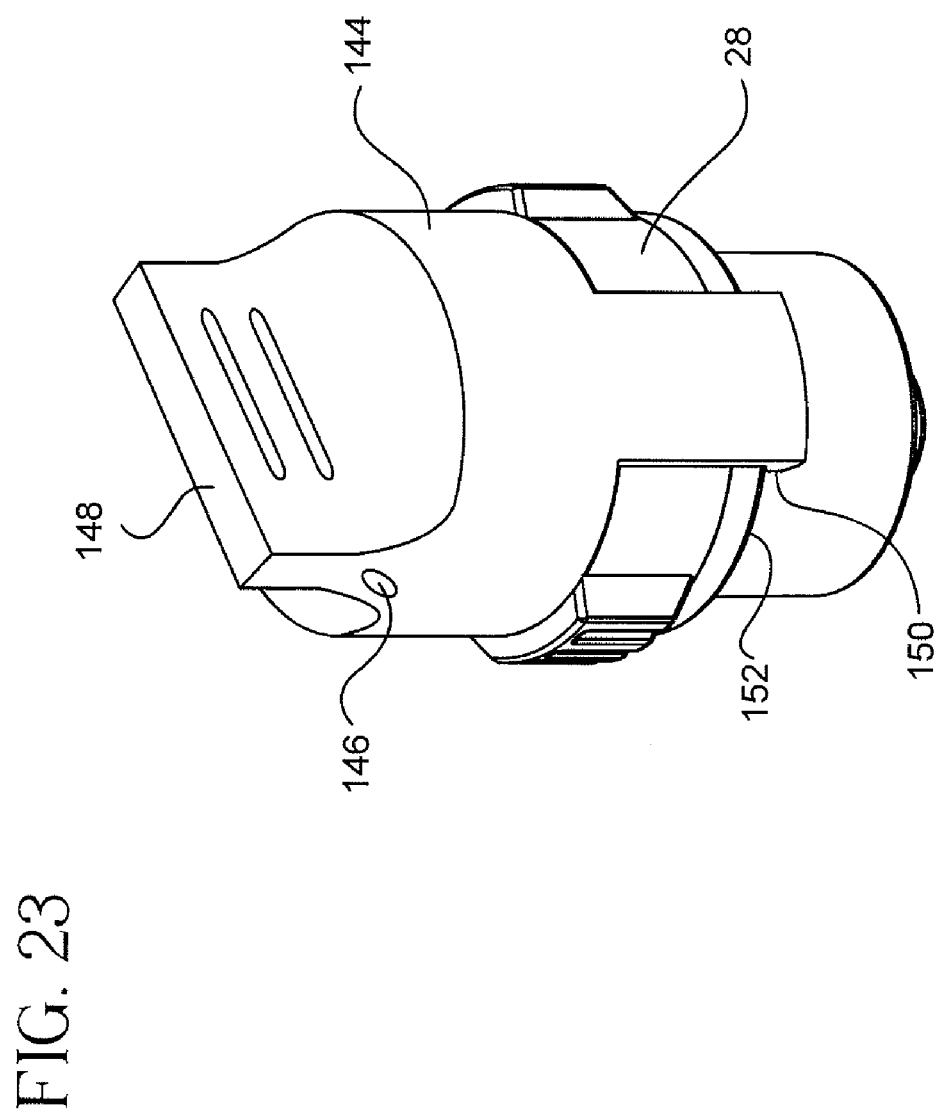
FIG. 23 is a perspective view of the vascular access device of FIG. 21 and a protective cover.

Referring now to FIG. 23, a perspective view of the vascular access device 28 of FIG. 22 is shown combined with a protective cover 144 including at least one vent hole 146 through the cover 144. The protective cover 144 is secured to the device 28 such that the top disc of the septum 30 is protected from microbial exposure. The protective cover 144 includes a finger grip 148 or other structure intended to enable an operator to be able to remove the protective cover 144 from the device 28 as desired. The protective cover 144 also includes at least one snap 150 capable of securing the protective cover 144 to a lower ledge 152 on the outer surface of the body of the device 28.

The protective cover 144 of the FIG. 23 may include the at least one needle 138 described with reference to FIGS. 21 and 22. For example, the protective cover may include two needles 138 at opposing ends of the finger grip 148, inserted within the vent holes 146 and secured to the protective cover 144. Thus, with the protective cover 144 engaged, or attached to, the device 28, the needle 138 will penetrate through the bottom disc 140 of the septum 30, providing a vent from the interior chamber of the device 28 to the external atmosphere in which the device 28 is placed. Alternatively, the protective cover 144 may not include any needle 138. Rather, an operator may insert any standard needle or any other device including a needle into the at least one vent hole 146 in order to vent the device 128. After any needle is removed from the device 28, the bottom disc 140 of the septum 30 will seal, preventing any further venting of fluid.

Figure 24:
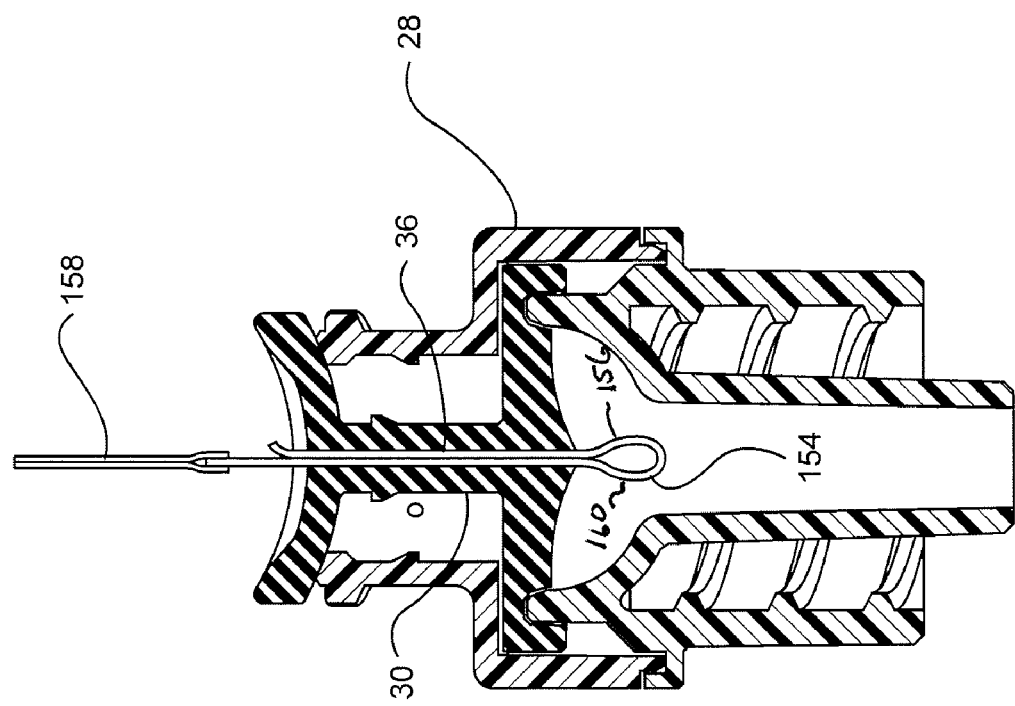
FIG. 24 is a cross section view of a vascular access device including a thread.
Figure 25:
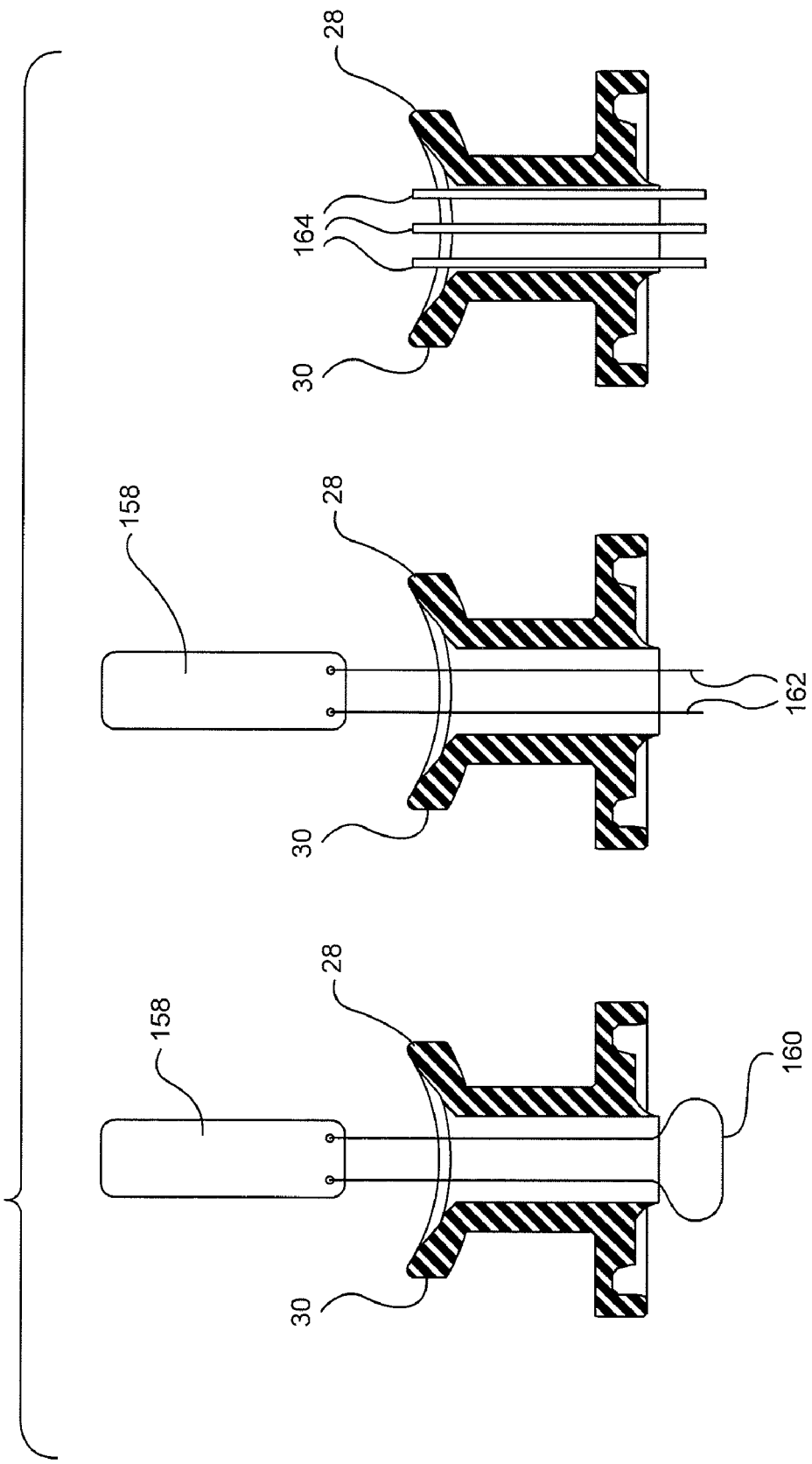
FIG. 25 is a series of cross section views illustrating various vascular access devices.

Referring now to FIG. 24 and FIG. 25, a vascular access device 28 may include a vent in communication with a septum 30. The vent may include a hydrophobic thread 154 placed within the slit 36 of the septum 30. Small airflow gaps 156 capable of venting gas from the device 28 into the external environment exist within the slit 36 and adjacent the thread 154. To inhibit the travel of fluid through the air flow gaps 156, the thread 154 may be a hydrophobic thread, such as a thread made of TEFLON™ material by DuPont.

The thread 154 may be connected to a pull tab 158 which enables an operator to remove the thread 154 from the slit 36 of the septum 30 after the device 28 is fully vented from gas residing therein. The thread 154 may be connected as a single thread by both ends to the pull tab 158 such that the thread forms a continuous loop 160. Alternatively, the pull tab 158 may be connected to one or more individual threads 162 that do not form a loop 160. Any number of loops 160 or individual threads 162 may be combined to form a single vent for the device 28.

Figure 26:
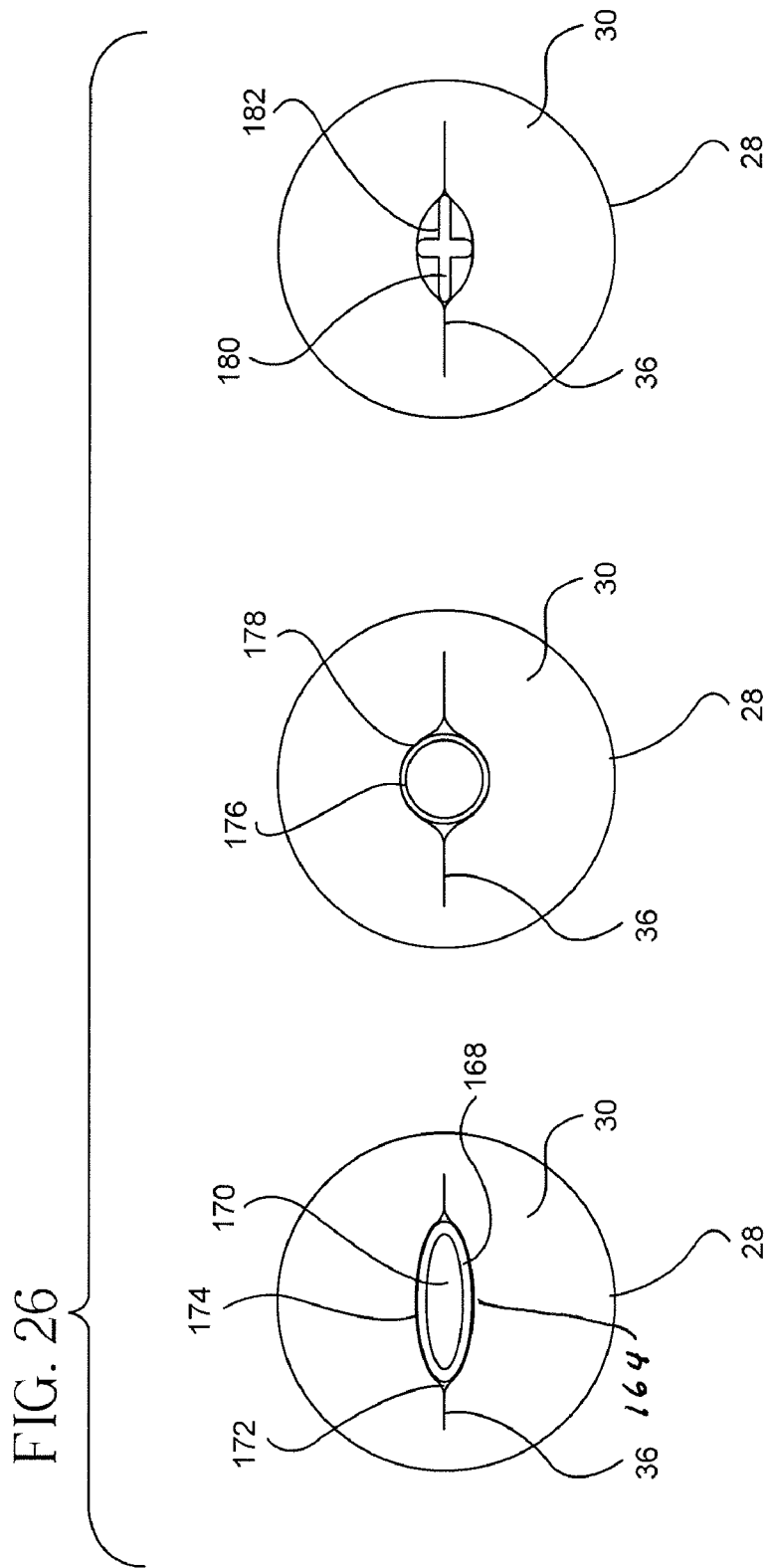
FIG. 26 includes top views of the septum of a vascular access device.

Referring now to FIG. 26, a vascular access device 28 may include a vent formed of a flexible plastic catheter tubing 164 in communication with a septum 30. The catheter tubing 164 may be formed of a soft plastic material that flattens or is otherwise compliant under the restorative force of the septum 30 along its slit 36. The inner lumen 166 of the at least one catheter 164 may include a hydrophobic surface and/or any venting material discussed throughout this disclosure.

A flattened cannula vent 168 may be inserted within the slit 36 of a septum 30 of a vascular access device 28. The flattened cannula vent may be formed of a flattened metal or other rigid cannula material and may include a similar hydrophobic or venting material within the lumen 170 of the cannula 168. The flattened cross section and rounded narrow corners 172 of the vent 168 will provide minimal stress 174 to the body of the septum 30. Under minimal or reduced stress 174, the septum 30 will be more likely to fully recover and seal after the cannula vent 168 is removed from the slit 36 of the septum 30.

A round cannula vent 176 may also be inserted within the slit 36 of a septum 30 of a vascular access device 28. The round cannula vent 176 will provide high stress 178 to the body of the septum 30 in contrast to the reduced or minimal stress 174 of the flattened cannula vent 168 shown in FIG. 28. A preferred cannula vent will provide minimal prolonged stress to the slit 36 and body of a septum 30 such that the septum 30 will be able to fully recover and seal after the cannula vent is removed from the slit 36.

A vascular access device 28 may also include a septum 30 with a vent inserted into the slit 36 of the septum 30. A cross section of the vent includes a substantially symmetrical cross 180 formation with a length that is greater than the width of the cross 180. The length of the cross 180 spans to near the full length of the slit 36. The width of the cross 180 provides structure capable of opening the slit 36 to an adequate degree capable of providing four sections of vent volume between each of the four ends of the cross 180 and the slit 36. Each of the ends of the cross 180 are rounded in order to prevent any damage or cutting into the material of the septum 30. The total vent volume between the cross 180 and the surfaces of the slit 36 will be adequate to vent air or other gas from an extravascular system 10 to which the device 28 is attached, and may include any venting material and/or hydrophobic material or surfaces thereon.

Because the cross 180 provides minimal opening of the slit 36 of the septum 30, it will minimize the amount of stress and consequently the memory of the body of the septum 30, permitting the septum to fully recover and become sealed after the cross 180 is removed from the device 28.

The cross 180 will thus provide less stress on the material of the septum 30 than the round cannula 176. The round cannula 176 will provide a higher level of stress 178 and consequently greater septum memory and more likelihood that leaks will occur within the slit 36 of the septum 30. If molded, the cross 180 will preferably be molded, such that the flash locations 182 will be located on any outer surface of the cross 180 that does not come into contact with the surface of the slit 36 of the septum 30. Thus, the remaining material at the flash locations 182 will be unable to damage the surface of the interior surface of the septum 30, causing rips, tears, or other actuations likely to damage or otherwise loosen or dislodge material from the septum 30.

Figure 27:
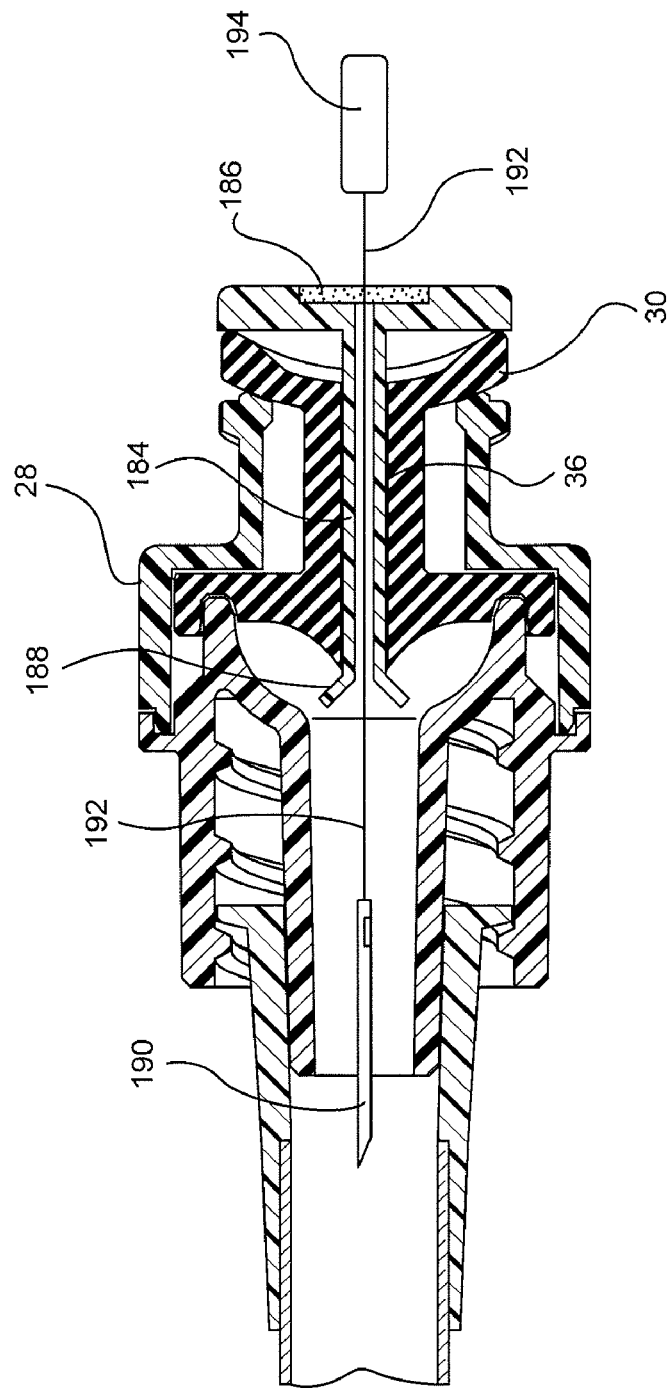
FIG. 27 is a cross section view of a vascular access device with a stylet and rigid tubing.

Referring now to FIG. 27, a vascular access device 28 includes a vent placed within the septum 30 of the device 28. The vent includes a rigid tubing 184 placed within the slit 36 of the septum 30 and connected to a venting membrane or venting plug 186 located on the exterior of the device 28. The internal end of the rigid tubing 184 or catheter may include a funnel 188 capable of receiving any structure 190 attached to the end of a stylet 192 that has been threaded through the lumen of the rigid tubing 184. The stylet 192 may be connected at its internal end to the structure 190 and at its external end to a puller 194.

During use, an operator may permit the device 28 to vent while the rigid tubing is inserted into the septum 30. After venting, the operator may pull the puller 194, causing the stylet 192 to pull the structure 190 through the funnel 188 of the rigid tubing 184, causing the rigid tubing 184, venting membrane 186, stylet 192 and structure 190 to be removed from the device 28. After these structures are removed from the device 28, the slit 36 of the septum 30 will return to its original resting, and sealed, position, preventing any additional gas and/or liquid from leaking through the septum 30 into the external environment.

Figure 28:
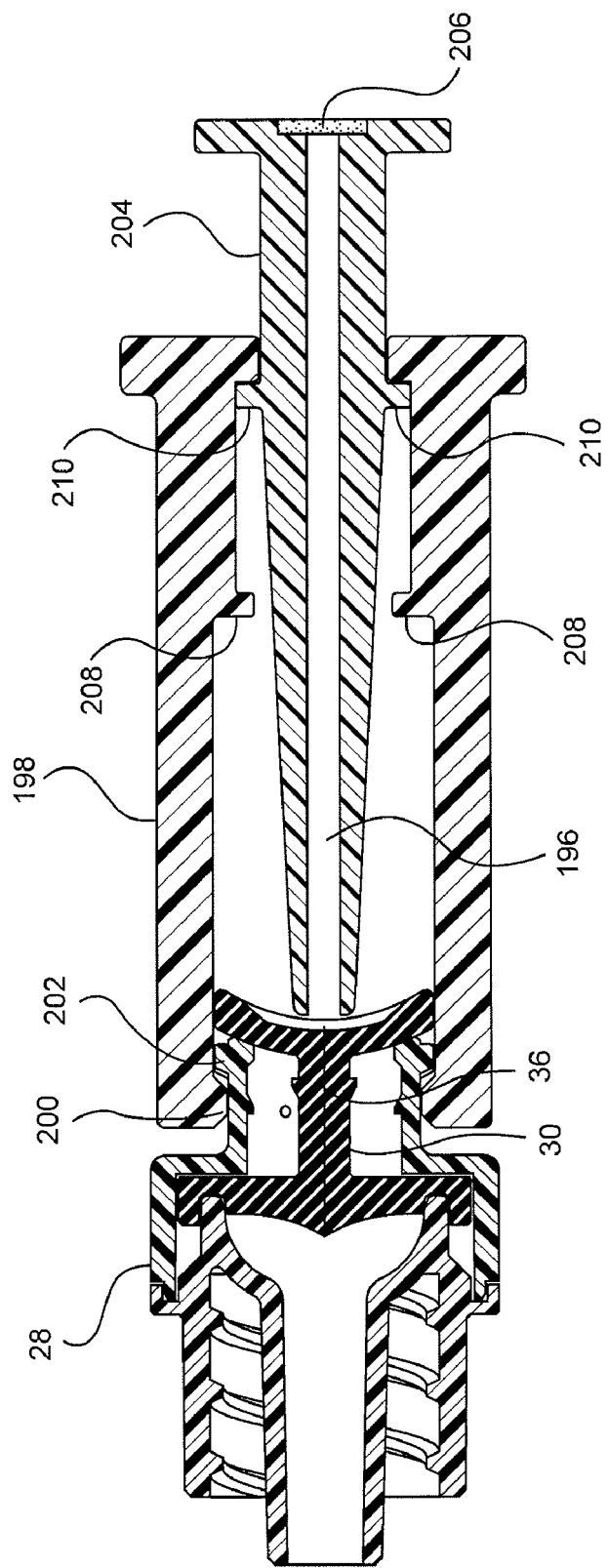
FIG. 28 is a cross section view of a vascular access device secured to a vent housing.

Referring now to FIG. 28, a vascular access device 28 may include a vent in communication with a septum 30. The vent includes an activatable venting channel 196 secured to the device 28 by means of a venting channel housing 198. The venting channel housing 198 may include threads 200 that correspond with threads 202 of the device 28. When the threads 200 are engaged with the threads 202, the housing 198 is secured to the device 28, placing a first end of the venting channel 196 in accessible communication with the slit 36 of the septum 30.

At a second end of the venting channel 196, a vent plug housing 204 that includes the venting channel 196 as its lumen, includes a vent plug or vent membrane 206. The vent plug or vent membrane 206 may include any venting material capable of permeability to gas but not liquid as discussed throughout this disclosure. The housing 198 may further include a vent activation stop 208 on its interior surface capable of stopping the vent channel housing 204 from advancing too far into and through the slit 36 of the septum 30. When the vent activation stop 208 comes into contact with a vent channel stop 210, the housing 204 will no longer advance into the device 28.

Thus, in use, an operator may advance the venting channel 196 into the slit 36 of the septum 30 to provide a means for venting gas from an extravascular system 10 to which the device 28 is attached. After venting is adequately accomplished, the operator may either remove the entire vent housing 198 from the device 28 or may retract the venting channel housing 204 from the septum 30. Once removed or retracted, the vent will leave the slit 36 of the septum 30 in a resting or sealed state capable of preventing any gas or liquid from escaping the device 28. The vent may be activated either by sliding the vent channel housing 204 or by screwing threads of the vent channel housing 204 into corresponding threads of the vent housing 198.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A medical connector device, comprising:
   a body, having an interior chamber and a first male connector end and a second female connector end, and a septum disposed within the interior chamber which is selectively actuated;
   a gas permeable vent capable of venting a gas from the interior chamber of the body to the exterior of the body; and
   a movable vent plug disposed within the gas permeable vent and being selectively movable to close the gas permeable vent to gas venting upon contact with the septum.

2. The medical connector device of claim 1, wherein the vent includes high-density polyethylene fibers.

3. The medical connector device of claim 1, wherein the vent plug includes a porous material.

4. The medical connector device of claim 1, wherein the male and female connectors are Luer connectors.

5. The medical connector device of claim 1, wherein the movable vent plug includes a solid portion and a gas permeable hydrophobic portion.

6. The medical connector device of claim 5, wherein the gas permeable hydrophobic portion extends from the interior chamber through the vent to the exterior of the body when the movable vent plug is in an open position.

7. The medical connector device of claim 6, wherein when the movable vent plug is in a closed position the gas permeable hydrophobic portion does not extend into the interior chamber and the solid portion of the vent plug covers the vent.

8. The medical connector device of claim 1, wherein the solid portion of the movable vent plug includes a sloped surface that responds to septum activation by moving the movable vent plug from an open position to a closed position.

9. The medical connector device of claim 8, wherein the sloped surface of the movable vent plug is in contact with the septum when the septum is not being actuated.

10. The medical connector device of claim 1, wherein the movable vent plug responds to an opening motion of the septum by moving in a lateral direction away from the septum opening.

11. The medical connector device of claim 1, comprising two vents and two movable vent plugs.

12. A method of venting a medical device, comprising:
providing a vascular access device comprising a body, having an interior chamber and a first male connector end and a second female connector end, and a septum disposed within the interior chamber which is selectively actuated;
providing a gas permeable vent capable of venting a gas from the interior chamber of the body to the exterior of the body;
providing a movable vent plug at least partially within the gas permeable vent;
venting gas through the gas permeable vent of the vascular access device; and
selectively closing the vent by activating the septum, such that contact between the septum and the vent plug closes the vent.

13. A medical connector device, comprising:
a body, having an interior chamber and a first male connector end and a second female connector end, and a septum disposed within the interior chamber which is selectively actuated;
a vent forming a fluid connection between the interior chamber and the exterior of the body; and
a movable vent plug disposed within the vent, the movable vent plug having a solid portion and a gas permeable hydrophobic portion, the gas permeable hydrophobic portion extending from the interior chamber through the vent when the movable vent plug is in an open position, and the solid portion of the vent plug covering the vent when the movable vent plug is in a closed position, wherein the solid portion of the vent plug includes a surface that responds to septum activation by moving the movable vent plug from the open position to the closed position.

* * * * *